(12) United States Patent
Watson et al.

(10) Patent No.: US 6,759,061 B2
(45) Date of Patent: Jul. 6, 2004

(54) LIVER FUNCTION IMPROVEMENT FORMULATION

(75) Inventors: Brenda F. Watson, Dunedin, FL (US); Leonard O. Smith, Gainesville, FL (US)

(73) Assignee: Renew Life, Inc., Clearwater, FL (US)

( * ) Notice: Subject to any disclaimer, the term of this patent is extended or adjusted under 35 U.S.C. 154(b) by 30 days.

(21) Appl. No.: 10/231,908

(22) Filed: Aug. 30, 2002

(65) Prior Publication Data

US 2003/0044512 A1 Mar. 6, 2003

Related U.S. Application Data

(60) Provisional application No. 60/316,542, filed on Aug. 31, 2001.

(51) Int. Cl.[7] .............................................. A61K 35/78
(52) U.S. Cl. ...................... 424/725; 424/756; 424/773; 424/774; 424/776; 424/777; 424/729; 424/702; 514/558; 514/561
(58) Field of Search ................................ 424/725, 756, 424/773, 774, 776, 777, 729, 702; 514/558, 561

(56) References Cited

U.S. PATENT DOCUMENTS

| | | | | |
|---|---|---|---|---|
| 5,728,735 A | * | 3/1998 | Ulrich et al. | |
| 5,830,455 A | * | 11/1998 | Valtuena et al. | |
| 6,126,942 A | * | 10/2000 | Yang | |
| 6,136,316 A | * | 10/2000 | Mehrotra et al. | |
| 6,136,859 A | * | 10/2000 | Henriksen | |
| 2002/0012708 A1 | * | 1/2002 | Ruepp | |

FOREIGN PATENT DOCUMENTS

JP          11246400 A    *   9/1999

OTHER PUBLICATIONS

Derwent English abstract of Chinese (CN) Pat. Appl. No. 1093532 A (1994).*
Derwent English abstract of Russian (RU) Pat. No. 2099960 C1 (1997).*
Derwent English abstract of Russian (RU) Pat. No. 2128515 C1 (1999).*
Hayashi et al. (Current Medical Research and Opinion (1999), vol. 15, No. 3, pp. 177–184).*

* cited by examiner

*Primary Examiner*—Francisco Prats
*Assistant Examiner*—Susan D. Coe
(74) *Attorney, Agent, or Firm*—MacMillan, Sobanski & Todd; Donald R. Fraser

(57) ABSTRACT

A food supplement formulation effective to improve the function of the liver comprises selenium, milk thistle seed, phosphatidyl choline, dandelion root, l-methionine, l-taurine, N-acetyl-cysteine, alpha lipoic arid, artichoke leaf, green tea leaf, turmeric root, belleric myrobalan fruit, boerhavia diffusa, eclipta alba, wedelolactones tinospora cordifolia, andrographis paniculata, and picrorhiza kurroa.

20 Claims, No Drawings

LIVER FUNCTION IMPROVEMENT FORMULATION

This application claims the benefit of U.S. provisional patent application Serial No. 60/316,542, filed Aug. 31, 2001.

FIELD OF THE INVENTION

The present invention relates generally to a liver function improvement formulation. More particularly, the invention is directed to a two-part organic food supplement formulation that improves the function of the human liver, by supporting the body's process for cleansing and detoxifying the liver.

BACKGROUND OF THE INVENTION

The liver is the largest human internal organ. It performs a number of functions, including detoxifying the body. The liver cleanses the body by filtering, or changing the compositions of toxins so that they can be removed from the blood stream, generally at a processing rate of about one liter of blood each minute. Endotoxins, exotoxins, and other wastes are directed to the kidneys or colon. A number of toxins, however, are made up of compounds that are difficult for the liver to filter and remove from the blood stream. These toxins are broken down by various enzymes so that they too may be removed from the body. Accordingly, a properly-functioning liver plays a critical role in determining a person's overall health.

It would be desirable to develop a food supplement which additionally improves the functioning of the human liver by promoting the body's ability to cleanse and detoxify the liver.

SUMMARY OF THE INVENTION

Accordant with the present invention, a beneficial; natural formulation that acts as a food supplement and assists in the cleansing and detoxification of the liver has surprisingly been discovered. The inventive food supplement comprises the following ingredients:
  selenium;
  milk thistle seed;
  phosphatidyl choline;
  dandelion root;
  l-methionine;
  l-taurine;
  N-acetyl-cysteine;
  alpha lipoic acid;
  artichoke leaf;
  green tea leaf;
  turmeric root;
  belleric myrobalan fruit;
  boerhavia diffusa;
  eclipta alba;
  wedelolactones;
  tinospora cordifolia;
  andrographis paniculata; and
  picrorhiza kurroa The organic formulation according to the present invention is useful as a food supplement to promote general health, and additionally is particularly useful for cleansing and detoxifying the liver for improved functionality.

DETAILED DESCRIPTION OF THE PREFERRED EMBODIMENT

The present invention is directed to a food supplement formulation, comprising selenium; milk thistle seed; phosphatidyl choline; dandelion root; l-methionine; l-taurine; n-acetyl-cysteine; alpha lipoic acid; artichoke leaf; green tea leaf; turmeric root; belleric myrobalan fruit; boerhavia diffusa; eclipta alba; wedelolactones; tinospora cordifolia; andrographis paniculata; and picrorhiza kurroa. The inventive food supplement formulation is administered in two parts. The first part is generally administered in the morning, while the second part is generally administered in the evening.

Selenium is a well-known component of several human enzymes that protects the body's arteries and cell membranes from damage from free radicals. Preferably, the concentration of selenium in part 1 of the inventive formulation may be about 0.1 weight percent.

Milk thistle seed is a bioflavonoid complex which exerts a powerful anti-oxidant effect, and interrupts the enterohepatic recirculation of toxins in the human liver. The concentration of milk thistle seed as a component of part 1 of the inventive formulation preferably may be about 25 weight percent.

Phosphatidyl choline is necessary for the body's production of acetycholine which assists the transmission of nerve impulses and breaks down fatty deposits in the blood stream. Phosphatidyl choline may be present in part 1 of the inventive formulation at a concentration preferably of about 15 weight percent.

Dandelion root is a well-known substance that stimulates the production of bile in the liver and the secretion of bile from the gallbladder, and is also a diuretic. Dandelion root may be present in part 1 of the inventive formulation at a concentration preferably of about 10 weight percent.

l-methionine is an amino acid and chelation agent that aids the break-down of fat in the human liver and arteries. The concentration of l-methionine as a component of part 1 of the inventive formulation preferably is about 10 weight percent.

l-taurine is an amino acid that assists in the production of bile, aids the absorption of fat-soluble vitamins, and supports healthy serum cholesterol levels. l-taurine may be present in part 1 of the inventive formulation at a concentration preferably of about 10 weight percent.

N-acetyl-cysteine is an altered form of the amino acid cysteine. N-acetyl-cysteine assists the body in breaking-down mucus and synthesizing glutathione, an important antioxidant. N-acetyl-cysteine may be present in part 1 of the inventive formulation at a concentration preferably of about 10 weight percent.

Alpha lipoic acid is a substance necessary for human metabolism, and additionally acts as an antioxidant when present in the human body in sufficient quantity. Preferably, the concentration of alpha lipoic acid as a component of part 1 of the inventive formulation may be about 5 weight percent.

Artichoke leaf is a well-known vegetable-derived component useful for the body's process of breaking-down fat, and for improving the production and flow of bile. Artichoke leaf may be present in part 1 of the inventive formulation at a concentration preferably of about 5 weight percent.

Green tea leaf contains polyphenols which are powerful antioxidants that additionally can increase the removal of cholesterol from the blood by a receptor mediated mechanism. Green tea leaf may be present in part 1 of the inventive formulation at a concentration preferably of about 5 weight percent.

Turmeric root is an antioxidant, and is reportedly useful for lowering cholesterol levels in the blood stream. The concentration of turmeric root in part 1 of the inventive formulation may be preferably about 5 weight percent.

Belleric myrobalan fruit is a natural product from the fruit of the terminalia bellerica plant, known to be useful for improving digestion, assisting in the body's nutrient absorption, and aiding the body's metabolic processes. Belleric myrobalan fruit may be present as a component of part 2 of the inventive formulation at a concentration preferably of about 20 weight percent.

Boerhavia diffusa is a plant-derived material known to be useful as a diuretic and anti-inflammatory compound. Boerhavia diffusa may be present as a component of part 2 of the inventive formulation at a concentration preferably of about 20 weight percent.

Eclipta alba is an herb used to promote bile flow and stimulate digestion. The concentration of eclipta alba as a component of part 2 of the inventive formulation may be preferably about 19 weight percent.

Wedelolactones is an extract from the eclipta alba plant, useful generally as an anti inflammatory agent. Wedelolactones may be present as a component of part 2 of the inventive formulation at a concentration preferably of about 1 weight percent.

Tinospora cordifolia is effective in inhibiting the growth of bacteria and enhancing immune resistance. Tinospora cordifolia may be present as a component of part 2 of the inventive formulation at a concentration preferably of about 20 weight percent.

Andrographis paniculata is a plant extract that enhances the body's immune system, and reportedly has been particularly effective for lessening the symptoms associated with the common cold. Preferably, andrographis paniculata may be present as a component of part 2 of the inventive formulation at a concentration preferably of about 10 weight percent.

Finally, Picrorhiza kurroa is a material widely used to treat dyspepsia and chronic diarrhea, and is effective as an antioxidant. Picrorhiza kurroa may be present as a component of part 2 of the inventive formulation at a concentration preferably of about 10 weight percent.

The aforementioned ingredients may be combined into parts 1 or 2 of the inventive formulation. Thereafter, the ingredients are mixed by conventional means to form parts 1 and 2 of the invention. Each of these parts may then be formed by conventional means into tablets for subsequent oral administration. Alternatively, the ingredients may be combined and placed in gelatin capsules, thereby forming separate capsules containing the part 1 and part 2 mixtures. The inventive formulation may also contain conventional food supplement adjuvants, fillers, and/or extenders such as, for example, rice flour.

Conveniently, the inventive food supplement formulation may be taken in separate oral dosages; part 1 in the morning, and part 2 in the evening. The dosage rates for parts 1 and 2 may vary over wide limits from about 100 mg each to about 5,000 mg each. Preferably, parts 1 and 2 are administered in dosages of about 1,000 mg each.

This invention is more easily comprehended by reference to the specific embodiments recited hereinabove which are representative of the invention. It must be understood, however, that the specific embodiments are provided only for the purpose of illustration, and that the invention may be practiced otherwise than as specifically illustrated without departing from its spirit and scope.

What is claimed is:

1. A food supplement formulation, comprising:
   a first part, comprising:
      selenium;
      milk thistle seed;
      phosphatidyl choline;
      dandelion root;
      l-methionine;
      l-taurine;
      N-acetyl-cysteine;
      alpha lipoic acid;
      artichoke leaf;
      green tea leaf; and
      turmeric root; and
   a second part, comprising:
      belleric myrobalan fruit;
      boerhavia diffusa;
      eclipta alba;
      wedelolactones;
      tinospora cordifolia;
      andrographis paniculata; and
      picrorhiza kurroa.

2. The food supplement formulation according to claim 1, wherein the concentration of selenium is about 0.1 weight percent of the total weight of the first part.

3. The food supplement formulation according to claim 1, wherein the concentration of milk thistle seed is about 25 weight percent of the total weight of the first part.

4. The food supplement formulation according to claim 1, wherein the concentration of phosphatidyl choline is about 15 weight percent of the total weight of the first part.

5. The food supplement formulation according to claim 1, wherein the concentration of dandelion root is about 10 weight percent of the total weight of the first part.

6. The food supplement formulation according to claim 1, wherein the concentration of l-methionine is about 10 weight percent of the total weight of the first part.

7. The food supplement formulation according to claim 1, wherein the concentration of l-taurine is about 10 weight percent of the total weight of the first part.

8. The food supplement formulation according to claim 1, wherein the concentration of N-acetyl-cysteine is about 10 weight percent of the total weight of the first part.

9. The food supplement formulation according to claim 1, wherein the concentration of alpha lipoic acid is about 5 weight percent of the total weight of the first part.

10. The food supplement formulation according to claim 1, wherein the concentration of artichoke leaf is about 5 weight percent of the total weight of the first part.

11. The food supplement formulation according to claim 1, wherein the concentration of green tea leaf is about 5 weight percent of the total weight of the first part.

12. The food supplement formulation according to claim 1, wherein the concentration of turmeric root is about 5 weight percent of the total weight of the first part.

13. The food supplement formulation according to claim 1, wherein the concentration of belleric myrobalan fruit is about 20 weight percent of the total weight of the second part.

14. The food supplement formulation according to claim 1, wherein the concentration of boerhavia diffusa is about 20 weight percent of the total weight of the second part.

15. The food supplement formulation according to claim 1, wherein the concentration of eclipta alba is about 19 weight percent of the total weight of the second part.

16. The food supplement formulation according to claim 1, wherein the concentration of wedelolactones is about 1 weight percent of the total weight of the second part.

17. The food supplement formulation according to claim 1, wherein the concentration of tinospora cordifolia is about 20 weight percent of the total weight of the second part.

18. The food supplement formulation according to claim 1, wherein the concentration of andrographis paniculata is about 10 weight percent of the total weight of the second part.

19. The food supplement formulation according to claim 1, wherein the concentration of picrorhiza kurroa is about 10 weight percent of the total weight of the second part.

20. A food supplement formulation, comprising:
- a first part; comprising:
  - about 0.1 weight percent selenium;
  - about 25 weight percent milk thistle seed;
  - about 15 weight percent phosphatidyl choline;
  - about 10 weight percent dandelion root;
  - about 10 weight percent l-methionine;
  - about 10 weight percent l-taurine;
  - about 10 weight percent N-acetyl-cysteine;
  - about 5 weight percent alpha lipoic acid;
  - about 5 weight percent artichoke leaf;
  - about 5 weight percent green tea leaf; and
  - about 5 weight percent turmeric root; and
- a second part, comprising:
  - about 20 weight percent belleric myrobalan fruit;
  - about 20 weight percent boerhavia diffusa;
  - about 19 weight percent eclipta alba;
  - about 1 weight percent wedelolactones;
  - about 20 weight percent tinospora cordifolia;
  - about 10 weight percent andrographis paniculata; and
  - about 10 weight percent picrorhiza kurroa.

* * * * *